United States Patent [19]

Miyoshi et al.

[11] Patent Number: 4,478,704
[45] Date of Patent: Oct. 23, 1984

[54] GAS DETECTION DEVICE

[75] Inventors: Tadahiko Miyoshi; Masanori Yoshikawa, both of Hitachi; Mitsuo Taguchi, Iwaki, all of Japan

[73] Assignee: Hitachi, Ltd., Tokyo, Japan

[21] Appl. No.: 454,487

[22] Filed: Dec. 29, 1982

[30] Foreign Application Priority Data

Jan. 11, 1982 [JP] Japan .................................. 57-1805

[51] Int. Cl.$^3$ .......................................... G01N 27/46
[52] U.S. Cl. .................... 204/412; 204/418; 204/424; 204/425; 204/426; 340/632
[58] Field of Search .............. 204/412, 431, 435, 433, 204/421, 424, 425, 426; 340/632

[56] References Cited

U.S. PATENT DOCUMENTS

| | | | |
|---|---|---|---|
| 3,909,384 | 9/1975 | Jasinski et al. | 204/412 |
| 3,996,123 | 12/1976 | Kruishoop | 204/409 X |
| 4,051,006 | 9/1977 | Neti et al. | 204/412 X |
| 4,057,478 | 11/1977 | Bruckenstein et al. | 204/412 X |
| 4,158,166 | 6/1979 | Isenberg | 204/426 X |
| 4,172,247 | 10/1979 | Ikeura | 204/424 X |
| 4,326,200 | 4/1982 | Bushman | 204/431 X |

FOREIGN PATENT DOCUMENTS 53-140098 12/1978 Japan .
54-148588 11/1979 Japan .
54-167790 11/1979 Japan .

Primary Examiner—G. L. Kaplan
Assistant Examiner—Nam X. Nguyen
Attorney, Agent, or Firm—Antonelli, Terry & Wands

[57] ABSTRACT

The gas detection offered by the present invention is characterized by the detection of CO as distinct from $H_2$. The optimum structure of the device therefor has an electrolytic cell wherein the electrode surfaces of a working electrode, a counter electrode and a reference electrode are kept in contact with electrolyte and wherein the open sides at both ends of the vessel containing the electrolyte are sealed by the working electrode, the counter electrode and the reference electrode; means for connecting between the working electrode and the counter electrode and means for applying a predetermined a voltage between the working electrode and the reference electrode, wherein sensitivity of the working electrode to carbon monoxide and hydrogen gas is smaller than that of the reference electrode.

16 Claims, 5 Drawing Figures

GAS DETECTION DEVICE

BACKGROUND OF THE INVENTION

1. Field of the Invention

The present invention relates to an electrochemical gas-detection device which is useful for detecting carbon monoxide gas (hereinafter referred to as CO) and/or hydrogen gas (hereinafter referred to as $H_2$) in the atmosphere.

2. Description of the Prior Art

Semiconductor sensors have widely been used for detecting gas in industry and in the home. However, these sensors have the disadvantages that the measurement precision thereof is liable to be affected by water vapor or other ambient gases, and that the sensitivity thereof is apt to change with time, etc. Accordingly, an electrochemical gas-detection method has been proposed in which chronoamperometry is used since it has a reliable measurement precision and sensitivity (see Japanese Official Gazettes for Laying-open of Patent Application No. 53-140098 (1978), Laying-open of Patent Application No. 54-148588 (1979), and Laying-open of Utility-Model Application No. 54-167790 (1979)). This method has the advantage that it is possible to make the quantitative analysis of the gas components, since the electrolytic current is proportional to the concentration of the gas components to be detected.

The electrochemical gas-detection method so far proposed has the disadvantage, however, when the gas component to be detected comes into contact with working electrode and reference electrode of the gas detecting device, the device is immediately responsive to $H_2$ and CO. This is because the working electrode and reference electrode of the conventional device have the same sensitivity to CO and $H_2$.

The conventional device cannot be used for detection of fuel gas leakage or detection of incomplete combustion. Accordingly the device cannot distinguish the gas leakage from combustion.

SUMMARY OF THE INVENTION

The purpose of the present invention is to provide a gas detection device of the type of electrochemistry which is highly reliable in the detection of CO and/or $H_2$.

The optimum structure of the device therefor has an electrolytic cell wherein the electrode surface of a working electrode, a counter electrode and a reference electrode are kept in contact with electrolyte and wherein the open sides at both ends of the vessel containing the electrolyte are sealed by the working electrode, the counter electrode and the reference electrode; means for connecting between the working electrode and the counter electrode and means for applying a predetermined voltage between the working electrode and the reference electrode, wherein sensitivity of the working electrode to carbon monoxide and hydrogen gas is smaller than that of the reference electrode.

The present inventors have discovered that when $H_2$ is in contact with the reference electrode the potential of the electrolyte in relation to the reference electrode is changed to make a polarization current flow toward the reduction side between the working electrode and the counter electrode, while such a phenomenon does not occur when CO is in contact with the reference electrode. Thus, it was found that when the optimum structure is applied, the oxidation current caused by $H_2$ is canceled by the effect of the polarization current, which enables a marked decrease in lowering the sensitivity to $H_2$. Furthermore, it was discovered that the optimum structure as above enables the discrimination of the type of gas by detecting the transitional flow of a polarization current flow toward the reduction side with the arrival of $H_2$, and by distinguishing this from the CO case when the polarization current can be disregarded.

For instance, the cell is provided with means for suppressing the arrival of the environmental gas at the working electrode so that the sensitivity of the working electrode is made smaller than that of the reference electrode. The surface area of the working electrode to be exposed to the environmental gas may be made smaller than that of the reference electrode.

PREFERRED EMBODIMENTS OF THE INVENTION

The present invention is further described by way of the embodiments thereof, but the invention is in no way limited by these embodiments.

In the following explanation, the atmosphere is taken as an example of the environmental gas.

Figure 1:
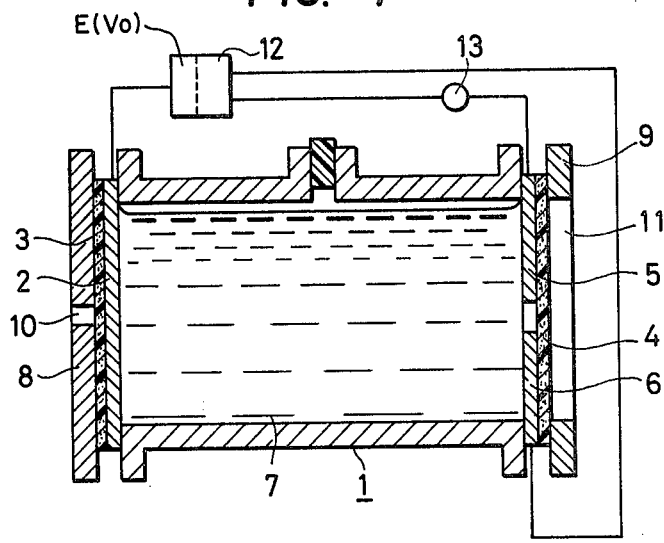
FIGS. 1, 4 and 5 are all drawings of the structures of gas detection devices according to the present invention.

FIG. 1 illustrates one embodiment of the gas detection device of the present invention. One end of an electrolytic cell 1 is sealed by a working electrode 2. The working electrode 2 is disposed on one surface of a gas-permeable porous membrane 3 having an electrical insulating property. In the same way, the other end of the electrolytic cell 1 is sealed by two electrodes disposed on one surface of a gas-permeable porous membrane 4, these are a counter electrode 5 and a reference electrode 6. The gas-permeable porous membranes 3 and 4 are made of a water-repellent and porous fluorinated synthetic resin such as Teflon (the same of a product of Dupont, U.S.). The three electrodes can each be prepared in the following way: the water-repellent porous membrane is coated with a paste prepared by mixing and kneading together a metallic powder and Teflon powder, for instance, and the membrane thus coated is dried, subjected to heat treatment and then shaped into a plate. More concretely, the membrane is coated to a thickness of 10-30 mg/cm² with a paste prepared by mixing 10-30% by weight of Teflon powder with platinum black or palladium black and is then subjected to pressure forming under a pressure of 50-1000 kg/cm² and then to heat treatment at a temperture of 200°-300° C. The main post of the vessel of the electrolytic cell 1 is made of a polycarbonate. The inside of the electrolytic cell 1 sealed in the above way is filled with an electrolyte 7. In the present embodiment, the electrolyte 7 is a solution, and more specifically, a normal solution of sulfuric or phosphoric acid of 2 to 16N is employed. Covers 8 and 9 are fitted over the outer sides of the gas-permeable porous membranes 3 and 4, respectively; the covers 8 and 9 are each provided with entrance holes 10 and 11. The entrance hole 10 is smaller in diameter than the entrance hole 11 that is equal in cross-sectional area to the inside of the electrolytic cell 1. More specifically, the entrance hole 10 has a diameter of 0.5 to 3 mm, while the entrance hole 11 has a diameter of 10 to 30 mm. The electrolytic cell 1 is a cylindrical vessel with an internal diameter of 10 to 40 mm and a length of 20 to 30 mm.

A voltage (Vo) is applied between the working electrode 2 and the reference electrode 6 which is stabilized by a potentiostat 12 and which causes the oxidation-reduction reaction of the component (CO) being detected. An ammeter 13 is connected between the potentiostat 12 and the counter electrode 5 to measure the electrolytic current flowing between the counter electrode 5 and the working electrode 2. The potentiostat 12 automatically controls a battery E so that the voltage between the working electrode 2 and the reference electrode 6 is always fixed (is not dependant on the current between the working electrode 2 and the counter electrode 5). The current flowing between the working electrode 2 and the counter electrode 5 becomes an output.

With this construction, the atmosphere arrives at the reference electrode 6 before arriving at the working electrode 2 owing to the relationship between the entrance holes 10 and 11.

The reference electrode 6 is used to show the oxidation-reduction potential of oxygen (hereinafter referred to as $O_2$) in the atmosphere, and the counter electrode 5 is devised to reduce $O_2$ in the atmosphere, and therefore the electrochemical reactions of CO and $H_2$ is as follows. That is, at the working electrode 2:

$$CO + H_2O \rightarrow CO_2 \uparrow + 2H^+ + 2e \qquad (1)$$

and $$H_2 \rightarrow 2H^+ + 2e \qquad (2)$$

while at the counter electrode 5:

$$O_2 + 4H^+ + 4e \rightarrow 2H_2O \qquad (3)$$

These reactions are assumed to occur at the interface of the electrolyte 7 with the metallic powder. The water-repellent porous membranes 3 and 4 pass the atmosphere to the electrode surfaces, preventing any leakage of liquid and maintaining the mechanical strength. To obtain the reaction shown by the above expression (1), it is especially desirable that the potential Vo of the working electrode 2 when it is based on the reference electrode 6 showing the oxidation-reduction potential of the $O_2$ is within the range of 0.2 to 0.5 V. In addition, it is desirable that the potential of the working electrode 2 is large, since a larger polarization current is induced by the $H_2$ with a larger potential of the electrode 2. However, when the potential is too large, the zero level (the leakage current when a raduction gas is absent) could become too large to detect the electrolytic current caused by CO gas.

Figure 2:
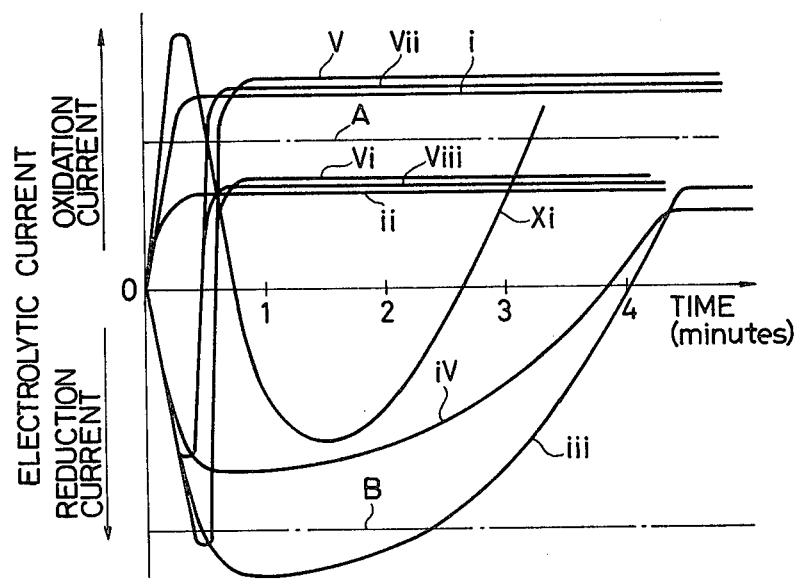
FIG. 2 is a graph showing the relationship between electrolytic currents generated by CO and $H_2$ and concentrations of the gases.

FIG. 2 shows the changes with time of the electrolytic current flowing between the working electrode 2 and the counter electrode 5 which is obtained by using an electrolytic cell 1 having the structure as shown in FIG. 1. The fixed voltage between the reference electrode 6 and the working electrode 2 is set at 0.2 V. There is also shown a curve xi of electrolytic current obtained by using a conventional sensor. In the figure, the curve i shows the output when a mixture of 200 ppm of CO and the balance being $N_2$ is used as the sample gas; the curve ii when a mixture of 100 ppm of CO and the balance being $N_2$ is used as the sample gas; the curve iii shows the output when 13000 ppm of $H_2$ is used as the sample gas, the curve iv when a mixture of 5000 ppm of $H_2$ and the balance being $N_2$ is used as the sample gas. As is clear from the figure, an oxidation current flows when CO is present, while the current flows to the reduction side when $H_2$ is present. This is presumably caused by the flow of a polarization current to the reduction side due to the change in potential of the reference electrode 6 which is caused by $H_2$ being in contact with the reference electrode 6 before contacting with the working electrode 2. The curve xi is provided as an example for comparison and will be explained later, since it refers to a different structure of electolytic cell. Further, in FIG. 2, the curve v shows the output when a mixture of 200 ppm of CO, 13000 ppm of $H_2$ and the balance being $N_2$ is used as the sample gas; the curve vi when a mixture of 100 ppm of CO and 13000 ppm of $H_2$ and the balance being $N_2$; the curve vii when a mixture of 200 ppm of CO and 5000 ppm of $H_2$ and the balance being $N_2$; the curve viii when a mixture of 100 ppm of CO and 5000 ppm of $H_2$ and the balance being $N_2$. The line A shows a critical line which is equivalent to a dangerous CO concentration of, such as, 150 ppm of CO, and the line B shows a critical line for dangerous $H_2$ concentration of, such as, 12500 ppm of $H_2$.

Figure 3:
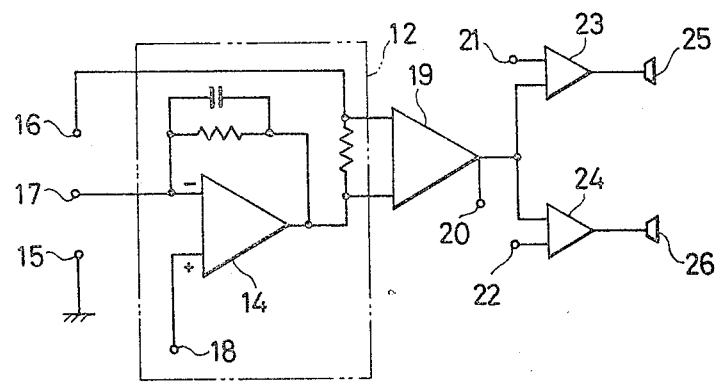
FIG. 3 is a circuit diagram of an embodiment of an alarm system employing the present invention.

A discrimination between $H_2$ and CO can now be done based on the electrolytic current in this way. FIG. 3 is a schematic illustration of a circuit which sounds an alarm by using this discrimination.

An operational amplifier 14 is provided inside the potentiostat 12. The working electrode 2, the counter electrode 5 and the reference electrode 6 are connected to a ground terminal 15, and terminals 16 and 17, respectively. The operational amplifier 14 has terminal 17 and another terminal 18 and a reference potential (negative potential) is given to terminal 18. A feedback circuit of a resistor and a capacitor is connected between, the output side and terminal 17 of the operational amplifier, and this circuit operates so that the potential of terminal 17 becomes equal to that of terminal 18. In this way the potential of the reference electrode 6 is kept at the reference potential, and a fixed potential difference is maintained between the working electrode 2 and the reference electrode 6. In addition, since a negative potential is given to terminal 18, the potential of the working electrode 2 connected to ground is kept high and that of the reference electrode 6 low. The operational amplifier is connected to ground, although this is not shown in the figure, and a closed circuit of the working electrode 2, terminal 15, ground, operational amplifier 14, terminal 16, counter electrode 5, electrolyte 7 and working electrode 2 is formed via ground. The output side of the operational amplifier 14 and terminal 16 are connected to an amplifier 19 through a resistor. Thus, changes in the electrolytic current appear at an output terminal 20. Terminals 21 and 22 give a comparison voltage to be compared with the output, and the outputs thereof are input via comparators 23 and 24 to buzzers 25 and 26, respectively. For instance, if a comparison voltage A corresponding to an oxidation current output is given to terminal 21, an alarm is sounded by the buzzer 25 only when the output voltage of terminal 20 becomes higher than the comparison voltage A. In this way, CO can be detected without any errors caused by the presence of $H_2$. At the same time, it is possible to detect the type of gas, whether it is CO or $H_2$, by the comparison voltage B corresponding to a reduction current output given to terminal 22. (For $H_2$ gas, a reduction current flows and thereby the buzzer 26 is sounded.) Furthermore, it is also possible to sound still another alarm according to differences in the density of the CO, with a comparison voltage C corresponding to another oxidation current output given to terminal 22.

Experimentation with different fixed potential differences Vo applied between the working electrode 2 and the reference electrode 6 has confirmed that the polarization current caused by $H_2$ increases with the increase in the fixed potential difference Vo, reducing the possibility of errors caused by the presence of $H_2$. Further it has been confirmed that a fixed potential difference of 0.1 V is sufficient to discriminate a CO concentration of 150 ppm, which must be detected sensitively by a general household gas sensor, from a $H_2$ concentration of 3000 ppm and that a fixed potential difference of at least 0.2 V is needed to discriminate a CO concentration of 150 ppm from a $H_2$ concentration of 12500 ppm (one-fourth of the density of LEL (lower explosive limit)). Moreover, it has also been confirmed that a rise in the zero level could make it difficult to measure an output when the fixed potential difference exceeds 0.5 V.

In the present invention, the alarm means is not limited to noise making device, but other means such as visual devices can be employed. Level of alarms (volume or tone of noises, brightness, etc.) may be varied in accordance with $H_2$ or CO. On the other hand, levels of alarms may be set in accordance with concentrations of $H_2$ or CO.

The following table shows the relationship between gas compartments in an environmental gas and operations of the detection device in the above mentioned example.

In the table, the dangerous $H_2$ concentration is optionally determined below the explosive limit (50000 ppm) in accordance with regulations or purposes; the concentration being 12500 ppm, for example. In the table, the dangerous CO concentration is set to 150 ppm for example. Human beings have toxic symptoms in an atmosphere containing 150 ppm of CO or more. When the concentration of CO exceeds 200 ppm, human beings will die within one hour.

TABLE

| CO concentration | $H_2$ concentration | | |
|---|---|---|---|
| | $\geq$ dangerous $H_2$ concentration | < dangerous $H_2$ concentration | zero |
| $\geq$ dangerous CO concentration | At first, reduction current larger than level B flows in the detection circuit to make noises by buzzer 26. Next, oxidation current larger than level A flows in the circuit to make noises by buzzer 25. (curve v) | At first, reduction current smaller than level B flows in the circuit which is not enough to make noises by buzzer 26. Next, oxidation current larger than level A flows in the circuit to make noises by buzzer 25. (curve vii) | Oxidation current larger than level A flows from the beginning in the circuit to make noises by buzzer 25. (curve i) |
| < dangerous CO concentration (not zero) | At first, reduction current larger than level B flows in the circuit to make noises by buzzer 26. Next, oxidation current smaller than level A flows in the circuit which is not enough to make noises by buzzer 25. (curve vi) | At first, reduction current smaller than level B flows in the circuit which is not enough to make noises by buzzer 26. Next, oxidation current smaller than level A flows in the circuit which in not enough to make noises by buzzer 25. (curve viii) | Oxidation current smaller than level A flows from the beginning in the circuit which is not enough to make noises by buzzer 25. (the curve ii) |
| zero | At first, reduction current larger than level B flows in the circuit to make noises by buzzer 26. Next, oxidation current smaller than level A flows in the circuit which is not enough to make noises by buzzer 25. (curve iii) | At first, reduction current smaller than level B flows in the circuit which is not enough to make noises by buzzer 26. Next, oxidation current smaller than level A flows in the circuit which is not enough to make noises by buzzer 25. (the curve iv) | No electrochemical reaction. |

The gas detection method and device of the present embodiment explained above have the advantage that they enable an extremely reliable detection of CO without any risk of errors caused by the presence of $H_2$. They have the secondary advantage that the device is very simple in the present embodiment, since the bleed holes 10 and 11 are the sole structure for delaying the time of arrival of the atmosphere at the working electrode 2. The water-repellent porous membranes 3 and 4 have, as said before, the effects of airing, of sealing in the liquid and of reinforcing the electrodes. Moreover, two kinds of alarm units attached have the effect that they enable the discrimination of different types of gas, and of the density thereof.

Figure 4:
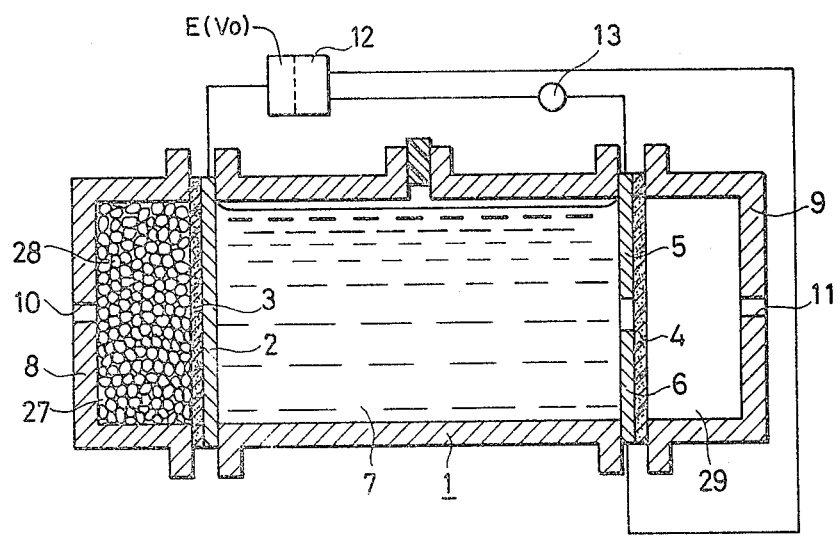

FIG. 4 is an illustration of a second embodiment of the present invention. The large difference thereof from the first embodiment is that gas chambers and a filler are provided. The same components as those shown in FIG. 1 are given the same reference numerals.

As is clear from the figure, the bleed hole 11 on the side of the reference electrode 6 is smaller than that in FIG. 1 and has the same diameter as that of the entrance hole 10 on the side of the working electrode 2. A gas chamber 27 filled with a filler 28 is provided on the side of the working electrode 2. A gas chamber 29 is also provided on the side of the reference electrode 6, but it is not filled with a filler. The gas chambers 27 and 29 are made to have the same sizes. The filler 28 is a gas adsorbent, more specifically, a mixture of silica gel and activated carbon in the ratio 1:1, and the adsorbent layer is made to be 2 mm thick.

Using this construction, the time of arrival of the atmosphere at the working electrode 2 can be made later than that at the reference electrode 6.

According to the present embodiment, the following effects are obtained from the employment of the gas adsorbent, in addition to the effects of the first embodiment. (1) Ethanol, acetic acid or similar gases which can cause errors, together with $H_2$, can be removed by adsorption, and (2) organic amines which cause the lowering of activity of the working electrode 2 can be removed and thereby the characteristics of the device can be kept stable for a long time. Accordingly, there is the advantage that the elimination of errors caused by various gases makes the device highly reliable. For this purpose, it is preferable that an adsorbent having a large specific surface area is employed. In addition, the gas adsorbent employed is not limited to the above, and so zeolite for instance may be employed, while the employment of an adsorbent on a carrier is also effective. Moreover, other fillers than the gas adsorbent may also be employed, if used only for the purpose of adjusting the time of arrival.

Figure 5:
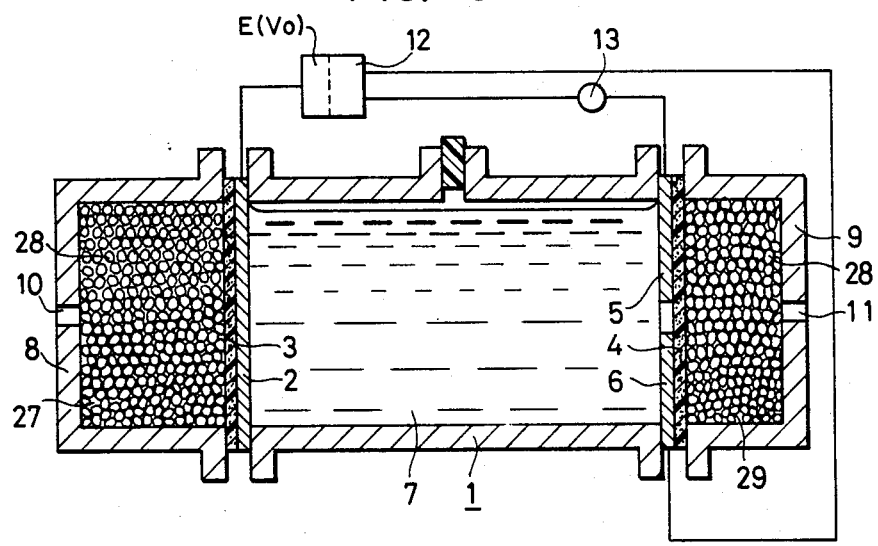

FIG. 5 is an illustration of a third embodiment of the present invention and the difference between this embodiment and the above second embodiment is that there is filler in both gas chambers. The same components as those shown in FIGS. 1 and 4 are given the same reference numerals.

As is clearly shown by the figure, the gas chamber 27 is made larger than the gas chamber 29, both being filled with the filler 28. The filler 28, which is effectively the same gas adsorbent as that in the second embodiment, is 1.5 to 3 times more in quantity in the gas chamber 27 than in the gas chamber 29. More concretely, the prescribed effect has been obtained consistently by making the filler layer in gas chamber 27 5 mm thick and by making the filler layer in gas chamber 29 2 mm thick.

By constituting the device as above, the time of arrival of the atmosphere at the working electrode 2 can also be delayed from that at the reference electrode 6.

According to the present embodiment, similar effects to those of the above second embodiment can be obtained as well. Experimentation has shown that the tendencies of the curves i to viii in FIG. 2 appear in the present embodiment as well.

If the filler in gas chamber 27 in the electrolytic cell 1 having the structure shown in FIG. 5 is remvoed as an experiment, the arrival of the atmosphere at the working electrode 2 is earlier than that at the reference electrode 6. In this case, the output in relation to CO is as shown by the curves i and ii in FIG. 2, while the output in relation to $H_2$ is as indicated by the curve xi. This presumably means that $H_2$ first arrives at the working electrode 2 and induces on oxidation current to flow, and that it arrives later at the reference electrode 6 and the large polarization current thus induced cancels the oxidation current. In this way, when the time of arrival of the atmosphere at the working electrode is made earlier, the oxidation current also flows at an early stage in relation to $H_2$, which results in errors.

When the filler 28 is also removed from the electrolytic cell 1 of FIG. 4, the time of arrival of the atmosphere is about the same in terms of the structure of the device. However, an adjustment of the time of arrival is possible by variations of the conditions of the position and angle of fitting of the gas detection device, the direction of air flow, etc. Accordingly, the structure of a device fitted for the gas detection method offered by the present invention is not limited to those in the above three embodiments. In addition, when $H_2$ and CO reach the gas detection device simultaneously, a reduction current generally flows at once and immediately after a current in the oxidation current direction flows, since $H_2$ has a higher velocity of diffusion than CO.

In all of the above three embodiments a solution is employed as the electrolyte. However, instead of a solution, sol or a solid electrolyte such as $H^+$ conducting solid electrolyte, for instance, are also effective in the present invention. The working electrode 2 and the reference electrode 6 can exchange each other for the purpose of the present invention. Moreover, to distinguish CO from $H_2$ and other gases (e.g. alcohol), it is also effective to remove or reduce the $H_2$ and other gases beforehand. As one means for removing or reducing the same, a method can be used wherein the components of the atmosphere are made to come into contact with catalysts before their arrival at the working electrode. For the purpose of removal and reduction of other various gases, $SnO_2$, $TiO_2$, CuO, or $Cr_2O_3$, etc. are effective as catalysts, and a method wherein the atmosphere is made to pass over a catalyst at a temperature of 100°–400° C., and reach the electrolytic cell thereafter, is practical.

As explained above, the present invention gives the effect that an extremely reliable detection of CO can be performed without any occurrance of errors caused by the presence of $H_2$.

What is claimed is:

1. In a gas detection device having an electrolytic cell including a working electrode, a counter electrode and a reference electrode, with one surface of each of the working electrode, counter electrode and reference electrode being kept in contact with an electrolyte, and another surface of each of the working electrode, the counter electrode and the reference electrode being exposed to an environmental gas, circuit means for electrically connecting said working electrode and said counter electrode to take out electric current due to electrochemical reaction, and means for applying a predetermined voltage between said working electrode and said reference electrode to detect carbon monoxide gas and/or hydrogen gas in the environmental gas, and further including means for suppressing the arrival of the environmental gas at said working electrode so that the sensitivity of said working electrode is made smaller than that of said reference electrode.

2. A gas detection device according to claim 1, wherein the means for suppressing comprises means for limiting the surface area of said working electrode exposed to said environmental gas so that the exposed surface area of said working electrode is made smaller than that of said reference electrode.

3. A gas detection device according to claim 1, wherein said another surface of said working electrode, said reference electrode and said counter electrode is covered with gas-permeable porous membranes having an electrical insulating property, each of said gas membranes having a cover thereover, the cover being provided with entrance holes, the dimension of said entrance hole in the cover for the membrane adjacent said working electrode being smaller than that of said entrance hole in the cover for the membrane adjacent the said reference electrode.

4. A gas detection device according to claim 1, wherein said predetermined voltage is set at the optimum value for the oxidation reaction of carbon monoxide at said working electrode.

5. A gas detection device according to claim 1, wherein said suppressing means is a layer of gas adsorbent which is provided adjacent the another surface of said working electrode.

6. A gas detection device according to claim 1, wherein there is provided a layer of a gas adsorbent adjacent said another surface of said reference electrode as well as adjacent said another surface of said working electrode.

7. A gas detection device according to claim 1, in which gas chambers, with entrance holes, are provided adjacent the another surface of said working electrode and adjacent the another surface of said reference electrode, and wherein the distance between said entrance hole and said working electrode is larger than the distance between said entrance hole and said reference electrode.

8. A gas detection device according to claim 7, in which at least said chamber adjacent the another surface said working electrode is filled with a filler.

9. A gas detection device according to claim 8, in which said filler is a gas adsorbent or a carrier supporting a gas adsorbent.

10. A gas detection device according to claim 9, in which said gas adsorbent is one of activated carbon, silica gel or zeolite.

11. A gas detection device according to claim 8, wherein only the chamber adjacent the another surface of said working electrode is filled with a filler.

12. A gas detection device according to claim 8, wherein both the chamber adjacent the another surface of said working electrode and the chamber adjacent the another surface of the reference electrode are filled with a filler, with the filler in the chamber adjacent the another surface of the working electrode being 1.5 to 3 times the amount in the chamber adjacent the another surface of the reference electrode.

13. A gas detection device according to claim 1, in which said predetermined voltage is within the range of 0.2 to 0.5 V.

14. A gas detection device according to claim 1, wherein both said counter electrode and said reference electrode contact one side of the electrolyte, and the working electrode contacts another side of the electrolyte.

15. A gas detection device comprising an electrolytic cell including a working electrode, a counter electrode and a reference electrode, with one surface of each of said working electrode, said counter electrode and said reference electrode being kept in contact with an electrolyte and with another surface of each of said working electrode, said counter electrode and said reference electrode being exposed to an environmental gas; circuit means for electrically connecting said working electrode and said counter electrode to take out an electric current due to electrochemical reaction; means for applying a predetermined voltage between said working electrode and said reference electrode to detect carbon monoxide gas and/or hydrogen gas in the environmental gas; means for measuring the electrolytic current flowing between said working electrode and said counter electrode; and means for signalling an alarm when the detected electric current due to carbon monoxide or hydrogen gas exceeds a predetermined value; and further including means for suppressing the arrival of the environmental gas at said working electrode so that the sensitivity of said working electrode is made smaller than that of said reference electrode, and wherein said voltage is set at the optimum value for the oxidation reaction of carbon monoxide at said working electrode.

16. A gas detection device according to claim 14, further including gas chambers adjacent the working electrode, on the one hand, and the counter electrode and reference electrode, on the other, with the gas chambers having entrance holes for passage of the environmental gas to the working electrode, counter electrode and reference electrode, and wherein the distance between the entrance hole in the gas chamber adjacent the working electrode, and the working electrode, is greater than the distance between the entrance hole in the gas chamber adjacent the reference electrode, and the reference electrode.

* * * * *